United States Patent [19]
Schnabel et al.

[11] Patent Number: 6,017,852
[45] Date of Patent: Jan. 25, 2000

[54] METHOD OF CONTROLLING UNDESIRED PLANT GROWTH IN RICE

[75] Inventors: Gerhard Schnabel, Grosswallstadt; Lothar Willms, Hofheim; Klaus Bauer, Hanau, all of Germany

[73] Assignee: Hoechst Schering AgrEvo GmbH, Berlin, Germany

[21] Appl. No.: 09/077,139

[22] PCT Filed: Nov. 4, 1996

[86] PCT No.: PCT/EP96/04798

§ 371 Date: May 21, 1998

§ 102(e) Date: May 21, 1998

[87] PCT Pub. No.: WO97/18711

PCT Pub. Date: May 29, 1997

[30] Foreign Application Priority Data

Nov. 23, 1995 [DE] Germany .................. 195 43 648

[51] Int. Cl.⁷ ............................ A01N 43/54; A01N 43/66
[52] U.S. Cl. ............................ 504/212; 504/214
[58] Field of Search ................. 504/212, 214; 544/211, 321, 332

[56] References Cited

U.S. PATENT DOCUMENTS

| | | | |
|---|---|---|---|
| 4,369,058 | 1/1983 | Levitt | 71/92 |
| 4,551,531 | 11/1985 | Meyer et al. | 544/320 |
| 4,632,695 | 12/1986 | Schurter et al. | 71/93 |
| 4,664,695 | 5/1987 | Schurter et al. | 71/92 |

FOREIGN PATENT DOCUMENTS

| | | |
|---|---|---|
| 0084020 A2 | 7/1983 | European Pat. Off. . |
| 0116518 A1 | 8/1984 | European Pat. Off. . |

Primary Examiner—S. Mark Clardy
Attorney, Agent, or Firm—Frommer Lawrence & Haug LLP

[57] ABSTRACT

The invention relates to a method of controlling harmful plants in rice crops, which comprises applying one or more compounds of the formula (I) or salts thereof

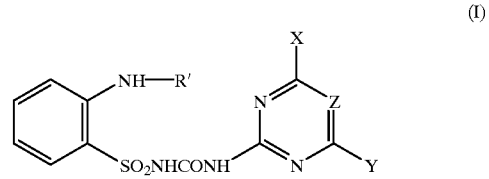

where $R^1$ is an acyl radical from the group $CO-R^2$, $CS-R^2$, $CO-OR^3$, $CS-OR^3$, $CO-SR^4$, $CS-SR^4$, $CO-NR^5R^6$ and $CS-NR^5R^6$, and $R^2$, $R^3$, $R^4$, $R^5$ and $R^6$ and also X, Y and Z are as defined in the formula (I) of claim 1, to the area under cultivation, which contains the harmful plants and rice plants or their seeds, in an effective amount of from 0.0001 to 0.5 kg of a.i./ha.

The compounds (I) are known per se. The invention also provides novel salts of the compounds (I).

6 Claims, No Drawings

METHOD OF CONTROLLING UNDESIRED PLANT GROWTH IN RICE

The invention is in the area of crop protection, in particular of the use of crop protection agents against monocotyledonous and dicotyledonous weeds in plant crops.

U.S. Pat. No. 4,369,058, U.S. Pat. No. 4,453,971 and U.S. Pat. No. 4,225,337 disclose N-acylated 2-aminophenylsulfonylureas, which are described as agents for controlling a wide range of mono- and dicotyledonous weeds. The sulfonylureas described are classified as herbicides having a wide activity against undesired plant growth at an application rate between 0.1 and 20 kg of active ingredient per hectare (kg of a.i./ha), preferably between 0.2 kg of a.i./ha and 10 kg of a.i./ha. According to the tests described in these publications, the compounds which were examined frequently do not have sufficient selectivity in crops of useful plants, i.e. the compounds cause considerable damage to the useful plants or have little if any herbicidal activity against harmful plants. According to the tests which have been described, the herbicidally active compounds in particular also cause considerable damage to the rice plants in rice crops.

Surprisingly, it has now been found that certain sulfonylurea herbicides have excellent selectivity in rice, and a pronounced activity against harmful plants which typically occur in rice crops is surprisingly retained even at low dosages of active compound. In particular perennial weeds encountered in the cultivation of rice which are often difficult to control, for example *Sagittaria spec., Cyperus serotinus, Scirpus maritimus, Eleocharis spec.* and *Scirpus juncoides*, and a wide range of annual weeds is controlled effectively. The sulfonylurea herbicides in question are therefore particularly suitable for controlling harmful plants in rice crops.

The present invention thus provides a method of controlling harmful plants in rice crops, which comprises applying one or more compounds of the formula (I) or salts thereof

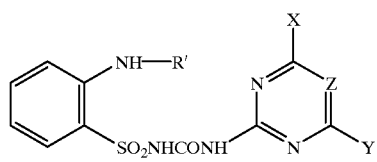

(I)

where

R$^1$ is an acyl radical from the group CO—R$^2$, CS—R$^2$, CO—OR$^3$, CS—OR$^3$, CO—SR$^4$, CS—SR$^4$, CO—NR$^5$R$^6$ and CS—NR$^5$R$^6$, R$^2$ is H, (C$_1$–C$_6$)alkyl, (C$_3$–C$_6$)cycloalkyl, (C$_3$–C$_6$) cycloalkyl-(C$_1$–C$_4$)alkyl, (C$_2$–C$_6$)alkenyl or (C$_2$–C$_6$) alkynyl, where each of the 5 last-mentioned radicals is unsubstituted or substituted by one or more radicals from the group halogen, (C$_1$–C$_4$)alkoxy, (C$_1$–C$_4$) haloalkoxy, (C$_1$–C$_4$)alkylthio, (C$_1$–C$_4$)haloalkylthio, CN, NH$_2$, mono- and di((C$_1$–C$_4$)alkylamino and, in the case of cyclic radicals, also by (C$_1$–C$_4$)alkyl and (C$_1$–C$_4$)haloalkyl, R$^3$ is a radical from the group of the radicals which are possible for R$^2$, except for H, R$^4$ is a radical from the group of the radicals which are possible for R$^3$, R$^5$,R$^6$ independently of one another are each a radical from the group of the radicals which are possible for R$^2$, or the group NR$^5$R$^6$ together is a substituted or unsubstituted 4-, 5- or 6-membered saturated or unsaturated heterocyclic radical which is bonded at the nitrogen atom, which, in addition to the nitrogen atom, contains no further hetero ring atom or further hetero ring atoms, preferably contains no or 1 or 2 hetero ring atoms from the group N, O and S, and which is unsubstituted or substituted by one or more radicals from the group (C$_1$–C$_4$)alkyl, (C$_1$–C$_4$)haloalkyl, halogen, (C$_1$–C$_4$) alkoxy and (C$_1$–C$_4$)haloalkoxy, X,Y independently of one another are halogen, (C$_1$–C$_6$) alkyl, (C$_1$–C$_6$)alkoxy, (C$_1$–C$_6$)alkylthio, where each of the three last-mentioned radicals is unsubstituted or substituted by one or more radicals from the group halogen, (C$_1$–C$_4$)alkoxy and (C$_1$–C$_4$)alkylthio, or is (C$_3$–C$_6$)cycloalkyl, (C$_3$–C$_6$)alkenyl, (C$_3$–C$_6$)alkynyl, (C$_3$–C$_6$)alkenyloxy or (C$_3$–C$_6$)alkynyloxy and Z is CH or N, to the area under cultivation, which contains the harmful plants and rice plants or their seeds, in an effective amount of from 0.0001 to 0.5 kg of a.i./ha, preferably 0.001 to 0.2 kg of a.i./ha, in particular 0.005 to 0.12 kg of a.i./ha.

Of particular interest are methods according to the invention using compounds of the formula (I) or salts thereof where R$^1$ is CO—R$^2$, CS—R$^2$, CO—OR$^3$, CS—OR$^3$, CO—SR$^4$, CS—SR$^4$, CO—NR$^5$R$^6$ and CS—NR$^5$R$^6$, preferably CO—R$^2$, CO—OR$^3$ or CO—NR$^5$R$^6$, R$^2$ is H, (C$_1$–C$_6$)alkyl, (C$_3$–C$_6$)cycloalkyl, (C$_3$–C$_6$) cycloalkyl-(C$_1$–C$_2$)alkyl, (C$_2$–C$_4$)alkenyl or (C$_2$–C$_4$) alkynyl, where each of the 5 last-mentioned radicals is unsubstituted or substituted by one or more radicals from the group halogen, (C$_1$–C$_3$)alkoxy, (C$_1$–C$_3$) haloalkoxy, (C$_1$–C$_3$)alkylthio, (C$_1$–C$_3$)haloalkylthio, CN, NH$_2$, mono- and di((C$_1$–C$_3$)alkylamino and, in the case of cyclic radicals, also (C$_1$–C$_4$)alkyl and (C$_1$–C$_4$) haloalkyl, R$^3$ is a radical from the group of the radicals which are possible for R$^2$, except for H, R$^4$ is a radical from the group of the radicals which are possible for R$^3$, R$^5$,R$^6$ independently of one another are each a radical from the group of the radicals which are possible for R$^2$, or the group NR$^5$R$^6$ together is a substituted or unsubstituted 4-, 5- or 6-membered saturated heterocyclic radical of the formula (A-1), (A-2), (A-3) or (A4)

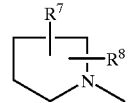

(A-1)

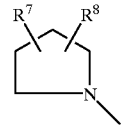

(A-2)

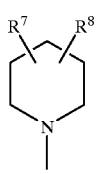

(A-3)

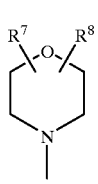

(A-4)

which is bonded at the nitrogen atom, $R^7R^8$ independently of one another are H, halogen, $(C_1-C_3)$alkyl, $(C_1-C_3)$haloalkyl, $(C_1-C_3)$alkoxy or $(C_1-C_3)$haloalkoxy, X,Y independently of one another are halogen, $(C_1-C_4)$alkyl, $(C_1-C_4)$alkoxy, $(C_1-C_4)$alkylthio, where each of the three last-mentioned radicals is unsubstituted or substituted by one or more radicals from the group halogen, $(C_1-C_4)$alkoxy and $(C_1-C_4)$alkylthio, or is $(C_3-C_6)$cycloalkyl, $(C_3-C_4)$alkenyl, $(C_3-C_4)$alkynyl, $(C_3-C_4)$alkenoxy or $(C_3-C_4)$alkynoxy and z is CH or N.

Preference is given to methods according to the invention using compounds of the formula (I) or salts thereof where $R^2$ is H, $(C_1-C_4)$alkyl, $(C_1-C_4)$haloalkyl, $(C_1-C_3)$alkoxy-$(C_1-C_4)$alkyl, $(C_1-C_3)$alkylthio-$(C_1-C_4)$alkyl, $(C_3-C_6)$cycloalkyl, $(C_3-C_6)$cycloalkylmethyl, preferably H, $(C_1-C_4)$alkyl or $(C_3-C_6)$cycloalkyl, in particular $C_2H_5$, i-$C_3H_7$ or cyclopropyl, $R^3$ is $(C_1-C_4)$alkyl, $(C_1-C_4)$haloalkyl, $(C_1-C_3)$alkoxy-$(C_1-C_4)$alkyl, $(C_1-C_3)$alkylthio-$(C_1-C_4)$alkyl, $(C_3-C_6)$cycloalkyl, $(C_3-C_6)$cycloalkylmethyl, $(C_3-C_4)$alkenyl or $(C_3-C_4)$alkynyl, preferably $(C_1-C_4)$alkyl or $(C_3-C_6)$cycloalkyl, in particular methyl or ethyl, $R^4$ is a radical from the group of the radicals which are possible for $R^3$, preferably $(C_1-C_4)$alkyl, $R^5,R^6$ independently of one another are H or $(C_1-C_4)$alkyl, one of the radicals X and Y is $(C_1-C_4)$alkyl, $(C_1-C_4)$alkoxy, $(C_1-C_4)$haloalkyl or $(C_1-C_4)$haloalkoxy, preferably methyl, methoxy or ethoxy, in particular methoxy, and the other of the radicals X and Y is halogen, $(C_1-C_4)$alkyl, $(C_1-C_4)$alkoxy, $(C_1-C_4)$alkylthio, where the three last-mentioned radicals are unsubstituted or substituted by one or more radicals from the group halogen, $(C_1-C_4)$alkoxy and $(C_1-C_4)$alkylthio, or is $(C_3-C_6)$cycloalkyl, $(C_2-C_4)$alkenyl, $(C_2-C_4)$alkynyl, $(C_3-C_4)$alkenoxy or $(C_3-C_4)$alkynoxy, preferably methyl, methoxy, ethoxy, chlorine, fluorine or $CF_3$, in particular methoxy, and Z is CH or N, in particular CH.

Particular preference is given to methods according to the invention using compounds of the abovementioned formula (I) or salts thereof where $R^1$ is CO—$R^2$ or CO—$OR^3$, for example $COOCH_3$, $COOC_2H_5$, COO-n-$C_3H_7$, COO-i-$C_3H_7$, COO-cyclo-$C_3H_5$, CO-$C_2H_5$, CO-n-$C_3H_5$, COO-i-$C_3H_7$ or CO-cyclo-$C_3H_7$.

In the formula (I) and in the formulae used hereinbelow, the radicals alkyl, alkoxy, haloalkyl, haloalkoxy, alkylamino and alkylthio and the corresponding unsaturated and/or substituted radicals may in each case be straight-chain or branched in the carbon skeleton. Unless specifically indicated, the lower carbon skeletons, for example those having 1 to 4 carbon atoms or, in the case of unsaturated groups, having 2 to 4 carbon atoms, are preferred for these radicals. Alkyl radicals, also in the composite meanings such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Alkenyl in the form "$(C_3-C_4)$alkenyl" or "$(C_3-C_6)$alkenyl" is preferably an alkenyl radical having 3 to 4 or 3 to 6 carbon atoms where the double bond is not between C-1 and C-2 (C-1 denotes the "yl" position); this applies correspondingly to $(C_3-C_6)$alkynyl or $(C_3-C_6)$alkynyl.

Halogen is, for example, fluorine, chlorine, bromine or iodine. Haloalkyl, aloalkenyl and haloalkynyl are alkyl, alkenyl and alkynyl, respectively, which are fully or partially substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

A heterocyclic radical or ring may be saturated, unsaturated or heteroaromatic; it contains one or more hetero ring atoms, preferably from the group N, O and S; it is preferably 5- or 6-membered and contains 1, 2 or 3 hetero ring atoms. The radical may, for example, be a heteroaromatic ring such as pyridyl, pyrimidinyl, pyridazinyl, pyrazinyl, thienyl, thiazolyl, oxazolyl, furyl, pyrrolyl, pyrazolyl and imidazolyl, inclusive of bicyclic or polycyclic aromatic or araliphatic compounds, for example quinolinyl, benzoxazolyl, etc., or else a partially or fully hydrogenated radical such as oxiranyl, pyrrolidyl, piperidyl, piperazinyl, dioxolanyl, morpholinyl, tetrahydrofuryl.

Suitable substituents for a substituted heterocyclic radical are the substituents mentioned further below, and additionally also oxo. The oxo group can also occur at the hetero ring atoms, which may exist in various oxidation stages, for example in the case of N and S.

Substituted radicals, such as substituted hydrocarbon radicals, for example substituted alkyl, alkenyl, alkynyl, aryl, phenyl and benzyl, or substituted heteroaryl, a substituted bicyclic radical or ring or a substituted bicyclic radical, optionally with aromatic moieties, are, for example, a substituted radical derived from the unsubstituted skeleton, the substituents being, for example, one or more, preferably 1, 2 or 3, radicals from the group halogen, alkoxy, haloalkoxy, alkylthio, hydroxyl, amino, nitro, cyano, azido, alkoxy carbonyl, alkylcarbonyl, formyl, carbamoyl, mono- and dialkylaminocarbonyl, substituted amino such as acylamino, mono- and dialkylamino, and alkylsulfynyl, haloalkylsulfynyl, alkylsulfonyl, haloalkylsulfonyl and, in the case of cyclic radicals, also alkyl and haloalkyl, and unsaturated aliphatic radicals, such as alkenyl, alkynyl, alkenyloxy, alkynyloxy, etc., which correspond to the above-mentioned saturated hydrocarbon-containing radicals. In the case of radicals having carbon atoms, preference is given to those having 1 to 4 carbon atoms, in particular 1 or 2 carbon atoms. Generally preferred are substituents from the group halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano. Particular preference is given to the substituents methyl, methoxy and chlorine.

The formula (I) also embraces individual stereoisomers and mixtures thereof. Such stereoisomers contain one or more asymmetric carbon atoms or else double bonds, which are not indicated separately in the formula (I). Depending on the specific spatial form, the possible stereoisomers are referred to as enantiomers, diastereomers, Z and E isomers, and they can be obtained by customary methods from mixtures of the stereoisomers or else by stereoselective reactions in combination with the use of stereochemically pure starting materials.

The compounds of the formula (I) can form salts where the hydrogen of the -$SO_2$-NH-group is replaced by a cation suitable for agriculture. These salts are, for example, metal salts, preferably alkali metal or alkaline earth metal salts, in particular sodium salts and potassium salts, or else ammonium salts or salts with organic amines. Salts can also be formed by adding an acid to basic groups, such as, for example, amino and alkylamino. Acids which are suitable for this purpose are strong inorganic and organic acids, for example HCl, HBr, $H_2SO_4$ or $HNO_3$.

The compounds of the formula (I) can be obtained by processes known from the literature (U.S. Pat. No. 4,369,058, U.S. Pat. No. 4,453,971, U.S. Pat. No. 4,225,237).

The salts of the compounds (I) according to the invention with bases are novel compounds. They also form part of the subject matter of this invention.

The salts of the compounds of the formula (I) are preferably prepared in inorganic or organic solvents which are inert under the preparation conditions, for example water, alcohols such as methanol, ketones such as acetone, optionally halogenated aliphatic or aromatic hydrocarbons such as heptane, dichloromethane, toluene or chlorobenzene or ethers such as tetrahydrofuran, at temperatures between the melting point and the boiling point of the solvent in question, preferably at temperatures from 0 to 100° C., by reaction of the sulfonylureas with acids or bases. Bases which are suitable for preparing the salts according to the invention are, for example, alkali metal carbonates, such as potassium carbonate, alkali metal and alkaline earth metal hydroxides, such as NaOH, KOH and Ca(OH)$_2$, ammonia or a suitable amine base, such as triethylamine or ethanolamine.

Acids which are suitable for salt formation have already been mentioned above.

The novel compounds of the formula (I) and the salts thereof have an outstanding herbicidal activity against a broad spectrum of economically important monocotyledonous and dicotyledonous weeds. The active compounds also act effectively against difficult-to-control perennial weeds which produce shoots from rhizomes, rootstocks or other perennial organs. In this context it does not matter whether the substances are applied before sowing, pre-emergence or post-emergence. Specifically, examples may be mentioned of some representatives of the monocotyledonous and dicotyledonous weed flora which can be controlled by the compounds according to the invention, without such mention being intended to restrict the invention to specific species.

Examples of monocotyledonous weed species against which the active compounds act effectively are Avena, Lolium, Alopecurus, Phalaris, Echinochloa, Digitaria, Setaria and Cyperus species from the annual group and, among the perennial species, Agropyron, Cynodon, Imperata and Sorghum and also perennial Cyperus species. In the case of dicotyledonous weed species, the spectrum of action extends to species such as, for example, Galium, Vioa, Veronica, Lamium, Stellaria, Amaranthus, Sinapis, Ipomoea, Matricaria, Abutilon and Sida among the annuals and Convolvulus, Cirsium, Rumex and Artemisia among the perennial weeds.

The novel active compounds also display outstanding control of weeds which occur under the specific growing conditions in rice, examples being Sagittaria, Alisma, Eleocharis, Scirpus and Cyperus.

Where the novel compounds are applied to the surface of the soil or into the dammed-up water in the cultivation of rice before germination, either the weed seedlings are prevented completely from emerging, or the weeds grow until they reach the cotyledon stage, but then stop growing and, finally, die off completely after three to four weeks have elapsed.

Where the active compounds are applied post-emergence to the green parts of plants, there is likewise a very rapid and drastic termination of growth after treatment, and the weed plants remain at the growth stage they were at at the time of application, or die off completely after a certain time, so that in this manner competition from weeds, which is damaging to the crop plants, is eliminated very early on and in a sustained manner.

Even though the compounds of the formula (I) or salts thereof have an excellent herbicidal activity with respect to monocotyledonous and dicotyledonous weeds, rice crops of sown or transplanted rice suffer only minimal or zero damage. For these reasons the present compounds are highly suitable for the selective control of unwanted plant growth in crops of agriculturally useful plants.

Furthermore, some of the compounds exhibit growth-regulating properties in rice plants. They intervene with a regulatory action in the endogenous plant metabolism and can therefore be employed for the targeted control of plant contents and for facilitating the harvest, for example by provoking desiccation and stunted growth or for generally controlling and inhibiting unwanted vegetative growth.

The compounds of the formula (I) or salts thereof can be applied in the customary formulations in the form of wettable powders, emulsifiable concentrates, sprayable solutions, dusts or granules. The invention therefore also provides herbicidal and plant growth-regulating compositions comprising the novel salts of compounds of the formula (I). The compounds of the formula (I) or salts thereof can be formulated in various ways depending on the prevailing biological and/or chemicophysical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes.

These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, for example insecticides, acaricides, other herbicides, fungicides, safeners, growth regulators, and/or fertilizers, for example in the form of a ready-mix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ether sulfates, alkanesulfonates, alkylbenzene-sulfonates, sodium ligninsulfonate, sodium 2,2'-dinaphthylmethane-6,6'-disulfonate, sodium dibutyl-naphthalenesulfonate or else sodium oleoylmethyltaurinate. To prepare the wettable powders, the herbicidal active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension conce ntrates can be water- or oil-based. They can be prepared, for exanple, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material.

The agrochemical formulations generally contain from 0.1 to 99% by weight, in particular from 0.1 to 95% by weight, of active compound of the formula (I) or salts thereof.

In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active ccmpound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, anti-foams, evaporation inhibitors and pH and viscosity regulators which are customary in each case.

Components which can be used in combination (co-components) for the novel active compounds in mixed formulations or in a tank mix are, for example, known active compounds, as described, for example, in Weed Research 26, 441–445 (1986), or "The Pesticide Manual", 9th edition, The British Crop Protection Council, 1990/91, Bracknell, England, and literature cited therein, for use in rice crops.

If appropriate, formulations present in commercial form are diluted in a customary manner for use, for example in the case of wettable powders, emulsifiable concentrates, dispersions and water-dispersible granules, with water, and they are subsequently applied to the plants, to parts of plants or to the soil which is used agriculturally or industrially, or to the area under cultivation on which the plants stand or where they grow or where they are present as seed. This includes special application variants which are customary in the cultivation of rice, for example application by watering where the herbicidal compositions are applied to the dammed up water of the irrigated area under cultivation. Preparations in the form of dusts, granules for soil application and broadcasting and sprayable solutions are usually not diluted with further inert substances prior to use.

The required application rate of the compounds of the formula (I) or salts thereof varies depending on external conditions such as temperature, humidity, the kind of herbicide used, etc. It may vary within wide limits, for example between 0.0001 and 0.5 kg/ha or more of active substance, but it is preferably between 0.005 and 0.12 kg/ha.

A. Chemical Examples

EXAMPLE A1

N-[(4,5-Dimethoxypyrimidin-2-yi)amino-carbonyl]-2-methoxycarbonylaminobenzene-sulfonamide (Table 1, Ex. No. 6)

3.0 g of 2-(methoxycarbonylamino)benzenesulfonamide and 7.1 g of 4,6-dimethoxy-2-(phenoxycarbonylamino)-pyrimidine are initially charged in 30 ml of acetonitrile, cooled to 0 to 5° C. and admixed with 4.9 ml of 1,8-diazabicyclo[5.4.0]undec-7-ene (DBU). After the reaction has ended, the mixture is concentrated and taken up in water. The mixture is washed with diethyl ether and the aqueous phase is acidified using concentrated hydrochloric acid (pH=1–2). The solid that separates off is purified by stirring with methanol and diisopropyl ether. This gives 4.5 g of the desired product (see title for A1); melting point: 195 to 196° C. (decomp.).

EXAMPLE A2

Sodium salt of N-[(4,6-dimethoxy-pyrimidin-2-yl)aminocarbonyl]-2-methoxycarbonylamino-benzenesulfonamide (Table 1, Ex. No. 9)

1.0 g of N-[(4,6-dimethoxypyrimidin-2-yl)-aminocarbonyl]-2-(methoxycarbonylamino)benzene-sulfonamide (Ex. Al) is initially charged in 20 ml of methylene chloride and admixed with 0.1 g of sodium hydroxide. After the reaction has ended, the mixture is concentrated under reduced pressure. This gives 1.1 g of the desired salt (see title for A2); melting point: 170–173° C. (decomp.).

The compounds listed in Table 1 below together with the products of the abovementioned examples A1 and A2 are obtained following Examples A1 and A2, or in a similar manner, if appropriate by using the processes mentioned in the general description. In Table 1, the abbreviations denote:

Ex. No.=example number/compound number
Mp.° C.=melting point in degrees Celsius
Me=methyl
Et=ethyl
Pr=n-propyl
n-Pr=n-propyl
i-Pr=isopropyl
c-Pr=cyclopropyl In the formula (la), "M" is covalently bonded H in the case of "H" and otherwise the equivalent of a cation of the formula given in Table 1, the positive charge not being indicated.

Some of the compounds could not be obtained in crystalline form or solvent-free and were identified by NMR spectroscopy.

TABLE 1

Compounds of the formula (Ia)

(Ia)

| Ex. No. | R$^1$ | M | X | Y | Z | Mp. ° C. |
|---|---|---|---|---|---|---|
| 1 | CO—H | H | OMe | OMe | CH | |
| 2 | CO—Me | H | " | " | " | |
| 3 | CO—Et | H | " | " | " | |
| 4 | CO-i-Pr | H | " | " | " | 160–182 (decomp.) |
| 5 | CO-c-Pr | H | " | " | " | 182 (decomp.) |
| 6 | CO—OMe | H | " | " | " | 195–196 (decomp.) |
| 7 | CO—OEt | H | " | " | " | |
| 8 | CO—O-i-Pr | H | " | " | " | |
| 9 | CO—OMe | Na | " | " | " | 170–173 (decomp.) |
| 10 | CO—OMe | K | " | " | " | |
| 11 | CO—OMe | H | OMe | Me | " | |
| 12 | CO—OMe | H | Me | Me | " | |
| 13 | CO-c-Pr | Na | OMe | OMe | " | |
| 14 | CO-c-Pr | K | " | " | " | |
| 15 | CO-i-Pr | Na | " | " | " | 205–206 (decomp.) |
| 16 | CO-i-Pr | K | " | " | " | |
| 17 | CO—OEt | Na | " | " | " | |
| 18 | CO—OEt | K | " | " | " | |
| 19 | CO—OMe | NH$_4$ | " | " | " | |
| 20 | CO—OMe | NMe$_4$ | " | " | " | |
| 21 | CO—OMe | NEt$_4$ | " | " | " | |
| 22 | CO—OMe | H | OEt | OMe | " | |
| 23 | CO-c-Pr | H | Me | Me | " | |
| 24 | CO-i-Pr | H | " | " | " | |
| 25 | CO-i-Pr | H | OEt | Me | " | |

TABLE 1-continued

Compounds of the formula (Ia)

(Ia)

[Structure: benzene ring with NH—R¹ substituent, SO₂—N(M)—CO—NH linked to a triazine ring bearing X, Y, Z substituents]

| Ex. No. | R¹ | M | X | Y | Z | Mp. ° C. |
|---|---|---|---|---|---|---|
| 26 | CO-i-Pr | H | OMe | Me | CH | |
| 27 | CO-i-Pr | Na | OMe | OEt | " | |
| 28 | CO-i-Pr | Na | OMe | Me | " | |
| 29 | CO-c-Pr | Na | OMe | OEt | " | |
| 30 | CO—CF₃ | H | OMe | OMe | " | |
| 31 | COCH₂Cl | H | " | " | " | |
| 32 | COCHCl₂ | H | " | " | " | |
| 33 | COCCl₃ | H | " | " | " | |
| 34 | COCH₂Br | H | " | " | " | |
| 35 | COOCH₂CCl₃ | H | " | " | " | |
| 36 | COOCH₂CH₂F | H | " | " | " | |
| 37 | COCH₂OCH₃ | H | " | " | " | |
| 38 | COCH₂SCH₃ | H | " | " | " | |
| 39 | COOMe | H | OMe | OMe | N | |
| 40 | COOMe | Na | " | " | " | |
| 41 | COOMe | H | Me | OMe | " | |
| 42 | CO-i-Pr | H | OMe | Me | " | |
| 43 | CO-i-Pr | H | OMe | OMe | " | |
| 44 | CO-c-Pr | H | OMe | Me | " | |
| 45 | CO-c-Pr | H | OMe | OMe | " | |

B. Formulation Examples a) A dusting agent is obtained by mixing 10 parts by weight of a compound of the formula (I) and 90 parts by weight of talc as inert substance and comminuting the mixture in a hammer mill.

b) A readily water-dispersible wettable powder is obtained by mixing 25 parts by weight of a compound of the formula (I), 64 parts by weight of kaolin-containing quartz as inert material, 10 parts by weight of potassium ligninsulfonate and 1 part by weight of sodium oleoylmethyltaurinate as wetting agent and dispersant and grinding the mixture in a pinned disk mill.

c) A readily water-dispersible dispersion concentrate is obtained by mixing 20 parts by weight of a compound of the formula (I) and 6 parts by weight of alkylphenol polyglycol ether (®Triton X 207), 3 parts by weight of isotridecanol polyglycol ether (8 EO) and 71 parts by weight of paraffinic mineral oil (boiling range for example from about 255 to over 277 ° C.) and grinding the mixture in a ball mill to a fineness below 5 microns.

d) An emulsifiable concentrate is obtained from 15 parts by weight of a compound of the formula (I), 75 parts by weight of cyclohexanone as solvent and 10 parts by weight of ethoxylated nonylphenol as emulsifier.

e) Water-dispersible granules are obtained by mixing 75 parts by weight of a compound of the formula (I),
10 parts by weight of calcium ligninsulfonate,
5 parts by weight of sodium lauryl sulfate,
3 parts by weight of polyvinyl alcohol, and
7 parts by weight of kaolin, grinding the mixture in a pinned disk mill and granulating the powder in a fluidized bed by spraying on water as granulation liquid.

f) Water-dispersible granules are also obtained by homogenizing and precomminuting 25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate, and
50 parts by weight of water, in a colloid mill, followed by grinding in a bead mill, and atomizing and drying the resulting suspension in a spray tower, using a single-substance nozzle.

C. Biological examples

Action on harmful plants in rice

Transplanted and sown rice and also typical rice weeds are cultivated in closed plastic pots in a greenhouse to the three-leaf stage (echinochloa 1.5-leaf) under paddy rice conditions (dammed height of water: 2–3 cm). This is followed by treatment with the compounds of the formula (I) or salts thereof. For this purpose, the formulated active compounds are suspended, dissolved or emulsified in water and applied by pouring them into the dammed water around the test plants in different dosages. After this treatment, the test plants are set up in a greenhouse under optimum growth conditions and are maintained under these conditions throughout the entire test period.

About three weeks after application, evaluation is made by visual rating of the damage to the plants by comparison with untreated controls, the compounds of the formula (I) and salts thereof exhibiting very good herbicidal activity against harmful plants which are typical for rice crops and damaging the rice plants to a negligible extent, if at all, in particular at low application rates. Some comparative compounds of very similar structure, however, surprisingly show no or considerably poorer selectivity. A number of test results are summarized in Table 2.

TABLE 2

Herbicidal activity and selectivity in rice

| Ex. | Dose g of a.i./ha | Herbicidal activity in % against | | | | | |
|---|---|---|---|---|---|---|---|
| | | ECHCG | SAGPY | ELOAC | CYPSE | ORSA/V | ORSA/S |
| 4 | 120 | 40 | 90 | 85 | 85 | 25 | 0 |
|   | 60  | 25 | 90 | 80 | 70 | 20 | 0 |
|   | 30  | 30 | 90 | 80 | 50 | 15 | 0 |
|   | 15  | 15 | 90 | 80 | 20 | 0  | 0 |
| 5 | 120 | 75 | 95 | 90 | 85 | 30 | 10 |
|   | 60  | 70 | 90 | 90 | 90 | 15 | 0 |
|   | 30  | 55 | 80 | 90 | 90 | 0  | 0 |
|   | 15  | 35 | 70 | 80 | 70 | 0  | 0 |
| 6 | 120 | 90 | 90 | 90 | 95 | 40 | 40 |
|   | 60  | 80 | 90 | 90 | 95 | 25 | 30 |
|   | 30  | 55 | 90 | 90 | 95 | 25 | 20 |
| 9 | 120 | 97 | 80 | 85 | 95 | 35 | 35 |
|   | 60  | 93 | 80 | 80 | 95 | 25 | 20 |
|   | 30  | 88 | 85 | 80 | 95 | 15 | 0 |
|   | 15  | 70 | 80 | 80 | 95 | 0  | 0 |
| 16 | 120 | 65 | 85 | 85 | 80 | 50 | 15 |
|    | 60  | 65 | 80 | 80 | 70 | 43 | 0 |
|    | 30  | 40 | 85 | 80 | 75 | 7  | 0 |
|    | 15  | 35 | 80 | 80 | 30 | 5  | 0 |
| C  | 120 | 96 | 80 | 88 | 90 | 80 | 80 |
|    | 60  | 98 | 70 | 85 | 85 | 80 | 75 |
|    | 30  | 95 | 70 | 80 | 85 | 70 | 65 |
|    | 15  | 95 | 70 | 70 | 80 | 65 | 60 |

Abbreviations for Table 2:
g of a.i./ha = gram of active ingredient per hectare, based on 100% pure active compound
ECHCG = *Echinochloa crus-galli*
SAGPY = *Sagittaria pygmaea*
ELEOAC = *Eleocharis acicularis*
CYPSE = *Cyperus serotinus*
ORYSA/V = *Oryza sativa* (transplanted), rice
ORYSA/S = *Oryza sativa* (sown), rice
Ex. (No.) = Example (number)/compound (number), where in the case of a simple number the example from Table 1 is designated by the same number
Ex. C = Comparative compound N-[(4,6-dimethoxypyrimidin-2-yl)-aminocarbonyl]-2-aminobenzene-sulfonamide

We claim:

1. A method of controlling harmful plants in rice crops, which comprises applying one or more compounds of the formula (I) or salts thereof (I)

where $R^1$ is an acyl radical from the group $CO-R^2$, $CS-R^2$, $CO-OR^3$, $CS-OR^3$, $CO-SR^4$, $CS-SR^4$, $CO-NR^5R^6$ and $CS-NR^5R^6$, $R^2$ is H, $(C_1-C_6)$alkyl, $(C_3-C_6)$cycloalkyl, $(C_3-C_6)$cycloalkyl-$(C_1-C_4)$alkyl, $(C_2-C_6)$alkenyl or $(C_2-C_6)$alkynyl, where each of the 5 last-mentioned radicals is unsubstituted or substituted by one or more radicals from the group halogen, $(C_1-C_4)$alkoxy, $(C_1-C_4)$haloalkoxy, $(C_1-C_4)$alkylthio, $(C_1-C_4)$haloalkylthio, CN, $NH_2$, mono- and di($(C_1-C_4)$alkylamino and, in the case of cyclic radicals, also $(C_1-C_4)$alkyl and $(C_1-C_4)$haloalkyl, $R^3$ is a radical from the group of the radicals which are possible $R^2$, except for H, $R^4$ is a radical from the group of the radicals which are possible for $R^3$, $R^5,R^6$ independently of one another are each a radical from the group of the radicals which are possible for $R^2$, or the group $NR^5R^6$ together is a substituted or unsubstituted 4-, 5-or 6-membered saturated or unsaturated heterocyclic radical which is bonded at the nitrogen atom, which, in addition to the nitrogen atom, contains no further hetero ring atom or further hetero ring atoms and which is unsubstituted or substituted by one or more radicals from the group $(C_1-C_4)$alkyl, $(C_1-C_4)$haloalkyl, halogen, $(C_1-C_4)$alkoxy and $(C_1-C_4)$haloalkoxy, X,Y independently of one another are halogen, $(C_1-C_6)$alkyl, $(C_1-C_6)$alkoxy, $(C_1-C_6)$alkylthio, where each of the three last-mentioned radicals is unsubstituted or substituted by one or more radicals from the group halogen, $(C_1-C_4)$alkoxy and $(C_1-C_4)$alkylthio, or is $(C_3-C_6)$cycloalkyl, $(C_3-C_6)$alkenyl, $(C_3-C_6)$alkynyl, $(C_3-C_6)$alkenyloxy or $(C_3-C_6)$alkynyloxy and z is CH or N, to the area under cultivation, which contains the harmful plants and rice plants or their seeds, in an effective amount of from 0.0001 to 0.5 kg of a.i./ha.

2. The method as claimed in claim 1, wherein $R^1$ is $CO-R^2$, $CS-R^2$, $CO-OR^3$, $CS-OR^3$, $CO-SR^4$, $CS-SR^4$, $CO-NR^5R^6$ and $CS-NR^5R^6$, $R^2$ is H, $(C_1-C_6)$alkyl, $(C_3-C_6)$cycloalkyl, $(C_3-C_6)$cycloalkyl-$(C_1-C_2)$alkyl, $(C_2-C_4)$alkenyl or $(C_2-C_4)$alkynyl, where each of the 5 last-mentioned radicals is unsubstituted or substituted by one or more radicals from the group halogen, $(C_1-C_3)$alkoxy, $(C_1-C_3)$haloalkoxy, $(C_1-C_3)$alkylthio, $(C_1-C_3)$haloalkylthio, CN, $NH_2$, mono- and di($(C_1-C_3)$alkylamino and, in the case of cyclic radicals, also by $(C_1-C_4)$alkyl and $(C_1-C_4)$haloalkyl, $R^3$ is a radical of the group of the radicals which are possible for $R^2$, except for H, $R^4$ is a radical from the group of the radicals which are possible for $R^3$, $R^5,R^6$ independently of one another are each a radical from the group of the radicals which are possible for $R^2$, or the group $NR^5R^6$ together is a substituted or unsubstituted 4-, 5-or 6-membered saturated heterocyclic radical of the formula (A-1), (A-2), (A-3) or (A4)

(A-1)

(A-2)

-continued

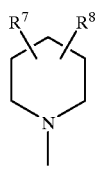

(A-3)

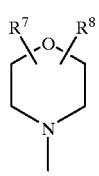

(A-4)

which is bonded at the nitrogen atom, $R^7R^8$ independently of one another are H, halogen, $(C_1-C_3)$alkyl, $(C_1-C_3)$haloalkyl, $(C_1-C_3)$alkoxy or $(C_1-C_3)$haloalkoxy, X,Y independently of one another are halogen, $(C_1-C_4)$alkyl, $(C_1-C_4)$alkoxy, $(C_1-C_4)$alkylthio, where each of the three last-mentioned radicals is unsubstituted or substituted by one or more radicals from the group halogen, $(C_1-C_4)$alkoxy and $(C_1-C_4)$alkylthio, or is $(C_3-C_6)$cycloalkyl, $(C_3-C_4)$alkenyl, $(C_3-C_4)$alkynyl, $(C_3-C_4)$alkenoxy or $(C_3-C_4)$alkynoxy and z is CH or N.

3. The method as claimed in claim 1, wherein $R^2$ is H, $(C_1-C_4)$alkyl, $(C_1-C_4)$haloalkyl, $(C_1-C_3)$alkoxy-$(C_1-C_4)$alkyl, $(C_1-C_3)$alkylthio-$(C_1-C_4)$alkyl, $(C_3-C_6)$cycloalkyl or $(C_3-C_6)$cycloalkylmethyl, $R^3$ is $(C_1-C_4)$alkyl, $(C_1-C_4)$haloalkyl, $(C_1-C_3)$alkoxy-$(C_1-C_4)$alkyl, $(C_1-C_3)$alkylthio-$(C_1-C_4)$alkyl, $(C_3-C_6)$cycloalkyl, $(C_3-C_6)$cycloalkylmethyl, $(C_3-C_4)$alkenyl or $(C_3-C_4)$alkynyl, $R^4$ is a radical from the group of the radicals which are possible for $R^3$, $R^5R^6$ independently of one another are H or $(C_1-C_4)$alkyl, one of the radicals X and Y is $(C_1-C_4)$alkyl, $(C_1-C_4)$alkoxy, $(C_1-C_4)$haloalkyl or $(C_1-C_4)$haloalkoxy, and the other of the radicals X and Y is halogen, $(C_1-C_4)$alkyl, $(C_1-C_4)$alkoxy, $(C_1-C_4)$alkylthio, where the three last-mentioned radicals are unsubstituted or substituted by one or more radicals from the group halogen, $(C_1-C_4)$alkoxy and $(C_1-C_4)$alkylthio, or is $(C_3-C_6)$cycloalkyl, $(C_2-C_4)$alkenyl, $(C_2-C_4)$alkynyl, $(C_3-C_4)$alkenoxy or $(C_{3-4})$alkynoxy and Z is CH or N.

4. The method as claimed in claim 1, wherein $R^1$ is $COR^2$ or $CO-OR^3$, $R^2$ is H, $(C_1-C_4)$alkyl or $(C_3-C_4)$cycloalkyl, $R^3$ is $(C_1-C_4)$alkyl or $(C_3-C_6)$cycloalkyl, one of the radicals X and Y is methoxy, ethoxy or methyl and the other of the radicals X and Y is methoxy, ethoxy, methyl, chlorine, fluorine or $CF_3$ and Z is CH or N.

5. The method as claimed in claim 4, wherein $R^2$ is ethyl, isopropyl or cyclopropyl, $R^3$ is methyl or ethyl, X,Y are each methoxy and Z is CH.

6. The method as claimed in claim 1, wherein the compounds (I) or salts thereof are applied to an application rate of 0.001 to 0.2 kg of a.i./ha.

* * * * *